United States Patent [19]

Volkov et al.

[11] 4,338,927
[45] Jul. 13, 1982

[54] DEVICE FOR RESTORING THE FUNCTION OF THE LOWER EXTREMITIES

[76] Inventors: Mstislav V. Volkov, Stroitelnaya ulitsa, 6, korpus 1, kv. 63; Oganes V. Oganesian, ulitsa Pervomaiskaya 74, kv. 87; Leonid A. Povarov, Tsvetnoi bulvar, 25, kv. 34, all of Moscow, U.S.S.R.

[21] Appl. No.: 243,804

[22] Filed: Mar. 16, 1981

[51] Int. Cl.³ .............................................. A61F 5/04
[52] U.S. Cl. ................................................ 128/92 A
[58] Field of Search ............. 128/92 A, 82, 83, 84 R, 128/84 B, 84 C, 69

[56] References Cited

U.S. PATENT DOCUMENTS

| | | | |
|---|---|---|---|
| 2,035,952 | 3/1936 | Ettinger | 128/92 A |
| 2,393,831 | 1/1946 | Stader | 128/92 A |
| 2,406,987 | 9/1946 | Anderson | 128/92 A |
| 4,185,623 | 1/1980 | Volkov et al. | 128/92 A |

*Primary Examiner*—John D. Yasko
*Attorney, Agent, or Firm*—Fleit & Jacobson

[57] ABSTRACT

The device of the invention comprises a mechanism for restoring the function of the ankle joint and a mechanism for correcting deformities of the foot. The mechanism for restoring the function of the ankle joint includes two pairs of half-rings, one of said pairs comprising an axial half-ring, which is fastened to the axle of rotation of the ankle joint, and a locking half-ring, which is fastened to the metatarsal bones of the foot, said half-rings being rigidly secured to each other. The other of said pairs includes a rotatable half-ring, which is fastened to the distal portion of the shin bone, and a locking half-ring, which is fastened to the middle portion of the shin bone, said half-rings being rigidly secured to each other. The mechanism for correcting deformities of the foot comprises brackets rigidly secured to the ends of the axial half-ring. The brackets carry spindles rotatably mounting L-shaped connecting rods. Corresponding ones of the arms of the L-shaped connecting rods are coupled with the ends of the locking half-ring fastened to the metatarsal bones of the foot, while respective ones of the arms of the connecting rods are coupled with the heel bone of the foot.

1 Claim, 2 Drawing Figures

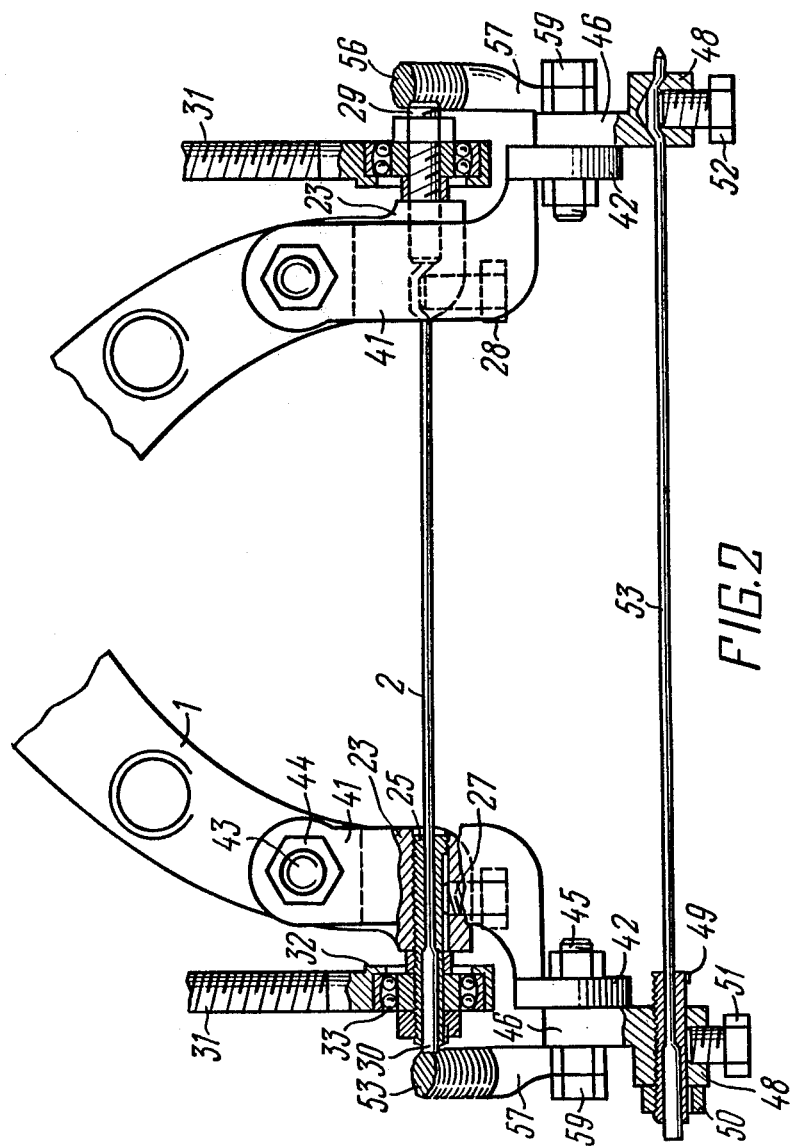

DEVICE FOR RESTORING THE FUNCTION OF THE LOWER EXTREMITIES

FIELD OF THE INVENTION

The invention relates to medical aids and appliances, and more particularly to a device for restoring the function of the lower extremities.

The device of the invention is applicable to the correction of talipes cavus, talipes varus, and talipes valgus.

DESCRIPTION OF THE PRIOR ART

Known in the art is a device for restoring the function of the foot which has a mechanism for restoring the function of the ankle joint (cf. the USSR Inventor's Certificate No. 474,171, Int.Cl.A61B 17/18, 1973).

In the known device, the mechanism for restoring the function of the ankle joint comprises two pairs of half-rings, one of said pairs comprising an axial half-ring, which is fastened to the axle of rotation of the ankle joint, and a locking half-ring, which is fastened to the metatarsal bones of the foot, said half-rings being rigidly secured to each other at their ends. The other of said pairs includes a rotatable half-ring, which is fastened to the distal portion of the shin bone, and a locking half-ring, which is fastened to the middle portion of the shin bone, said half-rings being rigidly secured to each other at their ends. The pairs of half-rings are interconnected by means of articulated distraction members. This device, however, cannot aid in correcting talipes cavus, talipes varus, and talipes valgus since it is void of construction elements with which the heel bone could be abducted.

SUMMARY OF THE INVENTION

It is an object of the present invention to provide a device for restoring the function of the lower extremities which could assist recovery of the shape and function of the foot.

This and other objects of the invention are attained in a device for restoring the function of the lower extremities comprising a mechanism for restoring the function of the ankle joint and a mechanism for correcting deformities of the foot, said mechanism for restoring the function of the ankle joint including two pairs of half-rings, one of said pairs comprising an axial half-ring, which is fastened to the axle of rotation of the ankle joint, and a locking half-ring, which is fastened to the metatarsal bones of the foot, said half-rings being rigidly secured to each other at their ends, the other of said pairs comprising a rotatable half-ring, which is fastened to the distal portion of the shin bone, and a locking half-ring, which is fastened to the middle portion of the shin bone, said half-rings being rigidly secured to each other at their ends, said mechanism for restoring the function of the ankle joint also including articulated distraction members mounted on the ends of said axial and rotatable half-rings and adapted to join together said pairs of half-rings, said mechanism for correcting deformities of the foot comprising brackets rigidly secured to the ends of the axial half-ring, spindles attached to said brackets, L-shaped connecting rods rotatably mounted on said spindles, ties to couple respective ones of the arms of said L-shaped connecting rods with the ends of the locking ring, which is fastened to the metatarsal bones of the foot, and a spoke that is driven through the heel bone of the foot and is attached to corresponding ones of the arms of said L-shaped connecting rods.

Important to the device are the brackets that are rigidly secured to the ends of the axial half-ring and have extended portions which can be aligned with the heel bone whose site corresponds with the anatomical position of the body, and the L-shaped connecting rods rotatably mounted on the brackets by virtue of the spindles; thus one can bring into a vertical plane the heel bone and respective arms of the connecting rods and drive through all of them a spoke that is fixed in spoke tightening members of the arms. The heel bone is abducted backward by rotating the nuts mounted on the ties, which thus perform in concert with each other a predetermined amount of oscillatory/translational motion towards the axial half-ring. This causes the L-shaped connecting rods to correspondingly rotate about the spindles, together with the arms and spoke. As a result, the heel bone assumes a site that corresponds with the anatomical position of the body.

BRIEF DESCRIPTION OF THE DRAWINGS

The invention will now be described in more detail, by way of example, with reference to the accompanying drawings, wherein:

FIG. 2 shows a partial lateral section of an axial half-ring and a mechanism for correcting deformities of the foot, according to the invention.

DETAILED DESCRIPTION OF THE INVENTION

Figure 1:
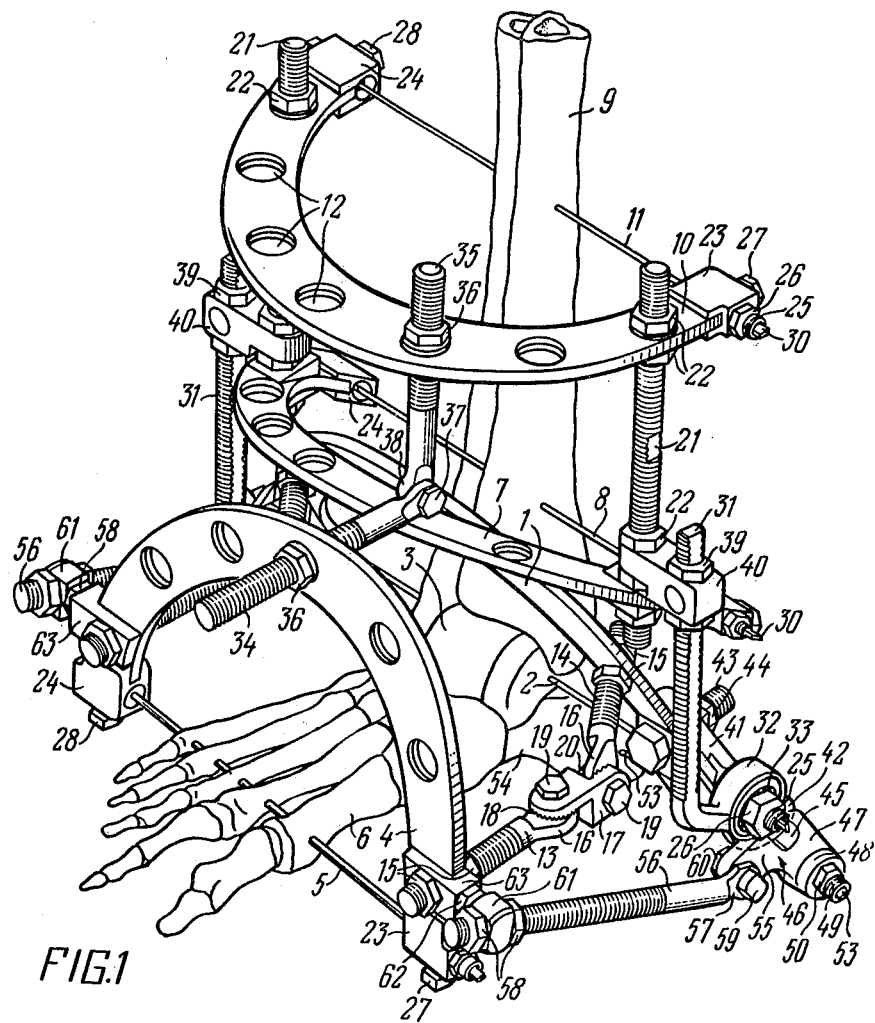
FIG. 1 shows a perspective view of a device for restoring the function of the lower extremities, according to the invention.

Referring now to FIG. 1, a device for restoring the function of the lower extremities comprises a mechanism for restoring the function of the ankle joint and, according to the invention, a mechanism for correcting deformities of the foot.

The mechanism for restoring the function of the ankle joint comprises two pairs of half-rings, one pair being articulated to the other. One of said pairs includes an axial half-ring 1, which is fastened to the axle of the ankle joint, which axle being implemented as a spoke 2 driven through the center of an ankle bone 3, and a locking half-ring 4, which is fastned to metatarsal bones 6 of the foot by means of a spoke 5. The other of said pairs comprises a rotatable half-ring 7, which is fastened to the distal portion of a shin bone 9 by means of a spoke 8, and a locking half-ring 10, which is fastened to the middle portion of the shin bone 9 by means of a spoke 11. The spokes 2, 5, 8, 11 are adapted to lie in frontal planes. The half-rings 1, 4, 7, 10 have at their circumferences equally spaced holes 12 which allow one to join these half-rings together. There are threaded studs 13 and 14 and nuts 15 by which the half-rings 1,4 are rigidly secured to each other at their ends. The threaded studs 13 and 14 have ears 16 and connect each other through the use of adapters 17 with serrations 18 and of bolts 19 and nuts 20. There is an angle between the studs 13,14 as viewed in a sagittal plane passing through them, a feature allowing for tilting the axial half-ring 1. The half-rings 7, 10 are rigidly secured to each other at their ends by means of threaded studs 21 and nuts 22. There are yokes 23, 24 at respective ends of the half-rings 1, 4, 7, 10. Fitted in the yokes 23 are threaded sleeves 25 provided with nuts 26. Each sleeve 25 has an axial taper bore and a flat extended throughout the overall length of the sleeve, a bolt 27 abutting against the flat. Fastening bolts 28 are screwed in the yokes 24. The yoke 24 of the axial half-ring 1 has a threaded sleeve 29 (FIG. 2). One end of each of the spokes 2,5,8,11 (FIG. 1) is pointed, while the other end has a broadened portion 30 mating the taper bore of the sleeve 25.

Articulated distraction members 31 provide a means for joining the two pairs of half-rings together. The members 31 has heads 32 that accommodate ball bearings 33. Another joining means for said pairs of half-rings are flexion/extension threaded bars 34, 35 and nuts 36. The bars 34, 35 connect each other through the use of a bolt 37 and a nut 38 and are adapted to pass through the holes 12 at the middle portions of the locking half-rings 4,10. The articulated distraction members 31 are coupled with the ends of the axial 1 and the locking half-ring 7 by means of the ball bearings 33, which fit over the sleeves 25, 29 of the axial half-ring 1. The threaded ends of the members 31 are provided with nuts 39 and fastened to extension plates 40. The latter are fastened to the ends of the rotatable half-ring 7 by means of the threaded studs 21 and nuts 22.

The mechanism for correcting deformities of the foot includes brackets 41 (FIG. 2) with discs 42, rigidly secured to the ends of the axial half-ring 1 with bolts 43 and nuts 44. The discs 42 are provided with spindles 45 which rotatably mount L-shaped connecting rods 46 each having an arm 47 (FIG. 1) with a lug 48 (FIG. 2). Fitted in the lugs 48 is a spoke tightening means which comprises a threaded sleeve 49, a nut 50, and fastening bolts 51, 52. The spoke tightening means carries a spoke 53 driven through a heel bone 54 (FIG. 1). The L-shaped connecting rods 46 have their arms 55 articulated to the ends of the locking half-ring 4 by means of ties 56 (FIG. 2) with ears 57 and nuts 58 (FIG. 1). The ties 56 have their ears 57 fastened to the arms 55 with bolts 59 and nuts 60, and have their other ends fastened to axles 61 with nuts 62. The axles 61 are fitted in plates 63 by means of articulated threaded studs 13 and nuts 15 at the ends of the locking half-ring 4.

PRINCIPLE OF OPERATION

The device of the invention is applied to the patient's foot in the following manner. First, the degree of the deformity of the foot and the amount of forward turning of the heel bone 54 are determined using the associated X-ray images. After that, the sites of the points through which the spokes 2, 5, 8, 11 are to be driven are marked using brilliant green, including the zone of the metatarsal bones 6, the center of the ankle bone 3, the heel bone 54, and the shin bone 9. To drive the spokes 2, 5, 8, 11 through the corresponding bones, use is made of an electric drill. The desirable spoke, together with its sleeve 25 fitted over it, is inserted in the head of the electric drill so that the broadened end thereof faces inward; the pointed end of the spoke is then applied under some pressure to the marked point on the extremity area of interest, the electric drill is energized and the extremity is transfixed with the spoke. Note that the spokes 2, 8, 11 driven respectively through the ankle bone 3 and the proximal and the middle portion of the shin bone 9 are situated in one frontal plane. After the spokes 2, 5, 8, 11 have been applied, the half-rings 1, 4, 7, 10 are fitted over them in such a manner that the pointed ends of these spokes sit in the yokes 24 and the sleeves 25 embracing the broadened portions 40 of the spokes 2,5, 8, 11 sit in the yokes 23. The sleeves 25 are fixed in place by the bolts 27 and the nuts 26 are screwed on the sleeves. The axial half-ring 1 is rigidly secured to the locking half-ring 4 by means of the threaded studs 13, 14, nuts 15, and adapters 17. A rigid connection between the studs 13 and 14 is attained by means of the serrations 18, bolts 19 and nuts 20. There is an angle between the studs 13, 14 as viewed in a sagittal plane passing through them, a feature allowing for tilting the half-ring 1, with the result that the latter does not touch the soft tissues of the foot and the shin. The rotatable half-ring 7 is rigidly secured to the locking half-ring 10 by means of the threaded studs 21 and nuts 22. At their middle portions, the locking half-rings 4, 10 connect each other using the flexion/extension threaded bars 34, 35 and nuts 36, the bars 34, 35 being coupled with each other by means of the bolt 37 and nut 38. When joining together the half-rings 7, 10, the extension plates 40 are set on the threaded studs 21 at the ends of the rotatable half-ring 7 and are fixed in place by the nuts 22. Mounted at the ends of the locking half-ring 4 are the plates 63 through which the threaded studs 13 pass. The sleeve 29 is screwed in the yoke 24 of the axial half-ring 1. The sleeves 25 and 29 mount the ball bearings 33, which are accommodated in the heads 32 of the articulated distraction members 31. The ends of the latter are fixed in the extension plates 40 by means of the nuts 39. To resist the suppuration of the soft tissues, the spokes 2, 5, 8, 11 in the half-rings 1, 4, 7, 10 must be held tight. For this purpose, the ends of the spokes 2, 5, 8, 11 are clamped by the fastening bolts 28 in the yokes 24 and the nuts 26 are then rotated to allow for translational motion of the sleeves 25 embracing the broadened end portions 30 of the spokes. On completion of the steps described above, the mechanism for correcting deformities of the foot is applied to the patient's foot in the following manner. The spoke 53 is driven through the heel bone 54 and the brackets 41 with the disks 42 are rigidly secured at the ends of the axial half-ring 1 in the holes 12 by means of the bolts 43 and nuts 44. The L-shaped connecting rods 46 are rotatably mounted on the disks 42 by means of spindles 45. The spoke 53 is fixed in the spoke tightening means in the lugs 48 of the arms 47 of the connecting rods 46, which tightening means comprises the sleeve 49, nut 50, and fastening bolts 51, 52. Note that the spoke 53 is driven through the heel bone with the sleeve 49 set on the spoke. The pointed end of the spoke 53 is clamped tight in the lug 48 of the L-shaped connecting rod 46 by the fastening bolt 52, the sleeve 49 embracing the broadened end portion of the spoke 53 is mounted in the lug 48 of the other L-shaped connecting rod 46, and the nut 50 is rotated to obtain the required tightening of the spoke. The arms 55 of the L-shaped connecting rods 46 mount the ties 56 by means of the ears 57, bolts 59, and nuts 60. The axles 61 are screwed in to the end faces of the plates 63 and are fixed in place by means of the nuts 62. Fitted in the axles 61 are the other ends of the ties 56 which are fixed by the nuts 58 but allowed to be moved in a longitudinal direction. The heel bone 54 is turned backward on account of translational motion of the ties 56 towards the axial half-ring 1 and resulting rotation of the L-shaped connecting rods 46 about the spindles 45, which carry the spoke 53 coupled with the heel bone 54.

What is claimed is:

1. A device for restoring the function of the lower extremities comprising:
 a mechanism for restoring the function of the ankle joint comprising:

two pairs of half-rings, one of said pairs including an axial half-ring, which is fastened to the axle of rotation of the ankle joint, and a locking half-ring, which is fastened to the metatarsal bones of the foot, said half-rings being rigidly secured to each other at their ends; the other of said pairs including a rotatable half-ring, which is fastened to the distal portion of the shin bone, and a locking half-ring, which is fastened to the middle portion of the shin bone, said half-rings being rigidly secured to each other;

articulated distraction members mounted on the ends of said axial and rotatable half-rings and adapted to join together said pairs of half-rings;

a mechanism for correcting deformities of the foot, comprising:

brackets rigidly secured to the ends of said axial half-ring;

spindles fastened to said brackets;

L-shaped connecting rods rotatably mounted on said spindles;

ties to couple respective ones of the arms of said L-shaped connecting rods with the ends of the locking half-ring, which is fastened to the metatarsal bones of the foot;

a spoke that is driven through the heel bone and is fastened to corresponding ones of the arms of said L-shaped connecting rods.

* * * * *